United States Patent
Baek (10) Patent No.: US 9,002,087 B2
(45) Date of Patent: Apr. 7, 2015

(54) METHOD AND APPARATUS FOR PROCESSING IMAGE, ULTRASOUND DIAGNOSIS APPARATUS, AND MEDICAL IMAGING SYSTEM

(75) Inventor: Ji-hye Baek, Gangwon-do (KR)

(73) Assignee: Samsung Medison Co., Ltd., Hongcheon-Gun (KR)

( * ) Notice: Subject to any disclaimer, the term of this patent is extended or adjusted under 35 U.S.C. 154(b) by 83 days.

(21) Appl. No.: 13/548,855

(22) Filed: Jul. 13, 2012

(65) Prior Publication Data

US 2013/0070993 A1   Mar. 21, 2013

(30) Foreign Application Priority Data

Sep. 19, 2011   (KR) .................. 10-2011-0094280

(51) Int. Cl.
| | | |
|---|---|---|
| *G06K 9/00* | (2006.01) | |
| *A61B 8/00* | (2006.01) | |
| *A61B 8/08* | (2006.01) | |
| *G06F 19/00* | (2011.01) | |
| *A61B 5/055* | (2006.01) | |
| *A61B 5/00* | (2006.01) | |

(52) U.S. Cl.
CPC .............. *A61B 8/466* (2013.01); *A61B 8/463* (2013.01); *A61B 8/467* (2013.01); *A61B 8/483* (2013.01); *A61B 8/523* (2013.01); *A61B 8/5261* (2013.01); *A61B 5/055* (2013.01); *G06F 19/321* (2013.01); *A61B 5/7425* (2013.01)

(58) Field of Classification Search
USPC ........................................... 382/131
See application file for complete search history.

(56) References Cited

U.S. PATENT DOCUMENTS

| | | | |
|---|---|---|---|
| 2008/0260226 A1* | 10/2008 | Moriya ...................... 382/128 |
| 2009/0022377 A1* | 1/2009 | Matsue et al. ............... 382/128 |
| 2009/0303252 A1 | 12/2009 | Hyun et al. | |
| 2011/0028844 A1 | 2/2011 | Hyun et al. | |
| 2011/0054324 A1 | 3/2011 | Lee | |
| 2012/0262453 A1* | 10/2012 | Endo et al. .................. 345/419 |

FOREIGN PATENT DOCUMENTS

| | | |
|---|---|---|
| JP | 2000-185036 A | 7/2000 |
| KR | 2009-0127091 A | 12/2009 |
| KR | 2010-0053071 A | 5/2010 |
| KR | 2011-0025706 A | 3/2011 |
| WO | WO-2011/074207 A1 | 6/2011 |

OTHER PUBLICATIONS

By Winter et al (Toward Registration of 3D Ultrasound and CT images of the Spine in Clinical Praxis: Design and Evaluation of Data Acquisition Protocol, Ultrasound in Medicine and Biology, New York, NY, US, vol. 35, No. 1, Nov. 1, 2009).*

(Continued)

*Primary Examiner* — Amara Abdi
(74) *Attorney, Agent, or Firm* — McDermott Will & Emery LLP (57) ABSTRACT

An image processing apparatus including an image data acquiring unit for acquiring ultrasound image data indicating information about an object; a standard image generating unit for generating an ultrasound standard image of the ultrasound image data; and a display unit for displaying the ultrasound standard image.

15 Claims, 7 Drawing Sheets

(56) References Cited

OTHER PUBLICATIONS

Winter et al (Toward Registration of 3D Ultrasound and CT images of the Spine in Clinical Praxis: Design and Evaluation of Data Acquisition Protocol, Ultrasound in Medicine and Biology, New York, NY, US, vol. 35, No. 1, Nov. 1, 2009).*

Extended European Search Report issued in European Patent Application No. 12161828.4 dated Aug. 6, 2012.

Winter, Susanne et al. "Toward Registration of 3D Ultrasound and CT Images of the Spine in Clinical Praxis: Design and Evaluation of a Data Acquisition Protocol." Ultrasound in Medicine & Biology. vol. 35 / No. 11. pp. 1773-1782. Jun. 2009.

Korean Notice of Allowance, w/ English translation thereof, issued in Korean Patent Application No. 10-2011-0094280 dted Jun. 26, 2013.

Korean Final Rejection, w/ English translation thereof, issued in Korean Patent Application No. KR 10-2011-0094280 dated Apr. 29, 2013.

Korean Office Action dated Oct. 23, 2012 from Korean Patent Application No. 10-2011-0094280.

European Office Action issued in European Application No. 12 161 828.4 issued Nov. 4, 2013.

* cited by examiner

METHOD AND APPARATUS FOR PROCESSING IMAGE, ULTRASOUND DIAGNOSIS APPARATUS, AND MEDICAL IMAGING SYSTEM

CROSS-REFERENCE TO RELATED PATENT APPLICATION

This application claims the benefit of Korean Patent Application No. 10-2011-0094280, filed on Sep. 19, 2011, in the Korean Intellectual Property Office, the disclosure of which is incorporated herein in its entirety by reference.

BACKGROUND OF THE INVENTION

1. Field of the Invention

The present invention relates to a method and apparatus for processing an image, an ultrasound diagnosis apparatus, and a medical image system.

2. Description of the Related Art

A diagnosis image of an object is obtained by an ultrasound diagnosis apparatus, a computed tomography (CT) system, a magnetic resonance imaging (MRI) system, or the like. In this case, in order to obtain a diagnosis image by using an ultrasound diagnosis apparatus, a user needs to scan a region of interest of an object by using a probe installed in the ultrasound diagnosis apparatus.

SUMMARY OF THE INVENTION

The present invention provides a method and apparatus for processing an image, an ultrasound diagnosis apparatus, and a medical image system which improve the accuracy of reading an ultrasound image. In addition, the present invention also provides a non-transitory computer readable recording medium having recorded thereon a program for executing the method in a computer. The technical objects of the present invention are not limited thereto and include other objects.

According to an aspect of the present invention, there is provided an image processing apparatus including an image data acquiring unit for acquiring ultrasound image data indicating information about an object; a standard image generating unit for generating an ultrasound standard image from the ultrasound image data based on a reference image with respect to at least one standard plane; and a display unit for displaying the ultrasound standard image.

According to another aspect of the present invention, there is provided an ultrasound diagnosis apparatus including a probe for acquiring ultrasound image data indicating information about an object; a main system for generating an ultrasound standard image from the ultrasound image data based on a reference image with respect to at least one standard plane; and a display unit for displaying the generated standard image.

According to another aspect of the present invention, there is provided a medical image system including a image processing apparatus for acquiring ultrasound image data indicating information about an object and for generating an ultrasound standard image from the ultrasound image data based on a reference image with respect to at least one standard plane; and a diagnosis unit for performing a diagnosis technique different from a diagnosis technique of acquiring the ultrasound image data, wherein the image processing apparatus displays the ultrasound standard image together with at least one comparison image that is generated by using the diagnosis technique different from a diagnosis technique of acquiring the ultrasound image data.

According to another aspect of the present invention, there is provided a method of processing an image, the method including acquiring ultrasound image data indicating information about an object; generating an ultrasound standard image from the generated ultrasound image data, based on a reference image with respect to at least one standard plane; and displaying the generated ultrasound standard image.

According to another aspect of the present invention, there is provided a method of displaying a diagnosis image, the method including obtaining a plurality of diagnosis images of an object, which are generated by at least two diagnosis apparatuses using different diagnosis techniques; and displaying together at least two diagnosis images from among the acquired plurality of diagnosis images.

According to another aspect of the present invention, there is provided a non-transitory computer readable recording medium having recorded thereon a program for executing the method of processing an image and the method of displaying a diagnosis image.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. Expressions such as "at least one of," when preceding a list of elements, modify the entire list of elements and do not modify the individual elements of the list.

Figure 1:
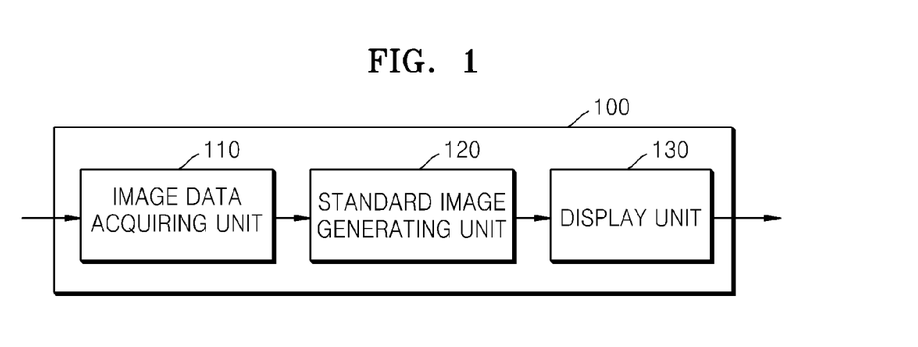
FIG. 1 is a block diagram of an image processing apparatus according to an embodiment of the present invention.

FIG. 1 is a block diagram of an image processing apparatus 100 according to an embodiment of the present invention.

Referring to FIG. 1, the image processing apparatus 100 includes an image data acquiring unit 110, a standard image generating unit 120, and a display unit 130.

Elements related to the present embodiment are illustrated in FIG. 1. However, it will be understood by those of ordinary skill in the art that besides the elements illustrated in FIG. 1 other general elements may be further included.

The standard image generating unit 120 of FIG. 1 may correspond to a single processor or a plurality of processors. The processor may be embodied with an array of a plurality of logic gates, or may be embodied with a combination of a general microprocessor and a memory where a program to be run in the microprocessor is stored. It will be also understood by those of ordinary skill in the art that it may be embodied with another form of hardware.

The image processing apparatus 100 processes an image of an object and provides the image to a user. In this case, the user is generally a medical expert such as a doctor, a nurse, or a medical image expert, but is not limited thereto. In addition, the object may be a human body, liver, heart, brain, abdomen, breasts, or the like, but is not limited thereto.

The image processing apparatus 100 may be installed in an ultrasound diagnosis apparatus (not shown), but is not limited thereto. That is, the image processing apparatus 100 may be installed in a general computer system, a laptop, a personal digital assistant (PDA), or the like.

The image data acquiring unit 110 acquires ultrasound image data indicating information regarding the object. For example, the image data acquiring unit 110 may acquire the ultrasound image data from an echo signal that is formed by reflecting an ultrasound signal transmitted to the object. Thus, the image data acquiring unit 110 may be, but is not limited to, a probe that acquires the echo signal that is reflected off the object and may acquire image data that is previously stored.

The standard image generating unit 120 generates an ultrasound standard image from the ultrasound image data that is acquired by the image data acquiring unit 110, based on a reference image with respect to at least one standard plane. For example, the standard image generating unit 120 may include a digital signal processor (DSP) (not shown) and a digital scan converter (DSC) (not shown). The DSP according to the present embodiment forms image data indicating a b-mode (brightness mode), c-mode (color mode), or d-mode (Doppler mode) by using the ultrasound image data acquired by the image data acquiring unit 110. The DSC according to the present embodiment generates an image that is scan-converted in order to display the image data that is formed by the DSP.

According to the present embodiment, the at least one standard plane corresponds to a standard plane that is used to diagnose the human body. For example, the at least one standard plane may include at least one of a sagittal plane, a coronal plane, and an axial plane, but is not limited thereto. The standard plane will be described below in detail with reference to FIG. 2.

A reference image according to the present embodiment may include at least one of a sagittal ultrasound image with respect to a sagittal plane, a coronal ultrasound image with respect to a coronal plane, and an axial ultrasound image with respect to an axial plane. The sagittal ultrasound image, the coronal ultrasound image, and the axial ultrasound image may be previously stored in a database (not shown), but are not limited thereto. That is, the sagittal ultrasound image, the coronal ultrasound image, and the axial ultrasound image may be acquired from an external source outside the image processing apparatus 100.

The standard image generating unit 120 may generate an ultrasound standard image with respect to at least one of the sagittal plane, the coronal plane, and the axial plane of the object, based on at least one of the sagittal ultrasound image, the coronal ultrasound image, and the axial ultrasound image.

For example, the standard image generating unit 120 may perform an image registration process on the ultrasound image data based on a reference image to generate an ultrasound standard image. In this case, the image registration process may be performed using an image registration algorithm. The image registration algorithm may include a mean squares metric technique, a normalized correlation metric technique, a mean reciprocal square difference technique, a mutual information metric technique, or the like.

In more detail, the image registration algorithm may include an image-based registration algorithm, a sensor-based global positing system (GPS) algorithm, or the like. The image-based registration algorithm may include a method of comparing intensities of images or comparing characteristics such as edges of images.

A method of generating a standard image by performing the image registration process on the ultrasound image data in the standard image generation unit 120 will be described below in detail with reference to FIGS. 3 and 4.

The standard image generating unit 120 may perform the image registration process based on the sagittal ultrasound image to generate an ultrasound standard image with respect to the sagittal plane of the object, may perform the image registration process based on the coronal ultrasound image to generate an ultrasound standard image with respect to the coronal plane of the object, or may perform the image registration process based on the axial ultrasound image to generate an ultrasound standard image with respect to the axial plane of the object.

According to the present embodiment, since the standard image generating unit 120 generates an ultrasound standard image, a standardized diagnosis image is used, thereby improving the accuracy of diagnosis of the object.

An ultrasound signal may be transmitted to the object and an ultrasound image may be obtained from an echo signal that is obtained by reflecting the transmitted ultrasound signal. In this case, an apparatus (for example, a probe) for transmitting the ultrasound signal to the object may be manipulated by a user. Thus, an ultrasound image of the object may be an ultrasound image of a region that is determined by a user's manipulation of the probe.

Thus, since the standard image generating unit 120 generates the ultrasound standard image, different ultrasound images may not be obtained with respect to the same region of interest according to the user's manipulation of the probe, thereby improving the accuracy of diagnosis.

The standard image generating unit 120 may generate the ultrasound standard image according to whether the ultrasound image data contains a region that is likely to have a disease. In this case, the region that is likely to have a disease may include a lesion, a mass, a tumor, and the like.

For example, the standard image generating unit 120 may analyze the ultrasound image data, may determine whether the ultrasound image data contains a region that is likely to have a disease, and may generate the ultrasound standard image only when the ultrasound image data contains the region that is likely to have a disease according to the determination result.

In this case, the standard image generating unit 120 may determine whether the ultrasound image data contains the region that is likely to have a disease by generating an ultrasound image or may determine whether image data on which beamforming is performed contains the region that is likely to have a disease.

Thus, when there is no region that is likely to have a disease in the object, the ultrasound standard image may be prevented from being generated unnecessarily.

However, the standard image generating unit 120 is not particularly limited. When a user wants screening using a standard plane, the standard image generating unit 120 may generate a standard image prior to diagnosing the user. That is, the standard image generating unit 120 may generate the ultrasound standard image regardless of whether there is a region that is likely to have a disease in the object and may diagnose the object by using the generated ultrasound standard image.

Thus, convenience for a user that is accustomed to diagnosis through diagnoisis image of diagnosis apparatuses other than the ultrasound diagnosis apparatus may be improved. In this case, the diagnosis apparatuses other than the ultrasound diagnosis apparatus may include a magnetic resonance imaging (MRI) system, a computed tomography (CT) system, a positron emission tomography (PET) system, or the like, but are not limited thereto.

In addition, the standard image generating unit 120 may automatically perform the above-described functions. That is, when the image data acquiring unit 110 acquires image data of the object, the standard image generating unit 120 may automatically generate the ultrasound standard image or may automatically determine whether there is a region that is likely to have a disease and may generate the ultrasound standard image.

The display unit 130 may display the ultrasound standard image generated by the standard image generating unit 120. For example, the display unit 130 may be an output device installed in the image processing apparatus 100, such as a monitor, a touch panel, a liquid crystal display (LCD), or the like, and a software module for driving the output device. Thus, the user may view the ultrasound standard image of the object through the display unit 130.

Since the image processing apparatus 100 generates the ultrasound standard image about the ultrasound image that may vary according to the user's manipulation of the probe, the user may easily and rapidly diagnose the object.

Figure 2:
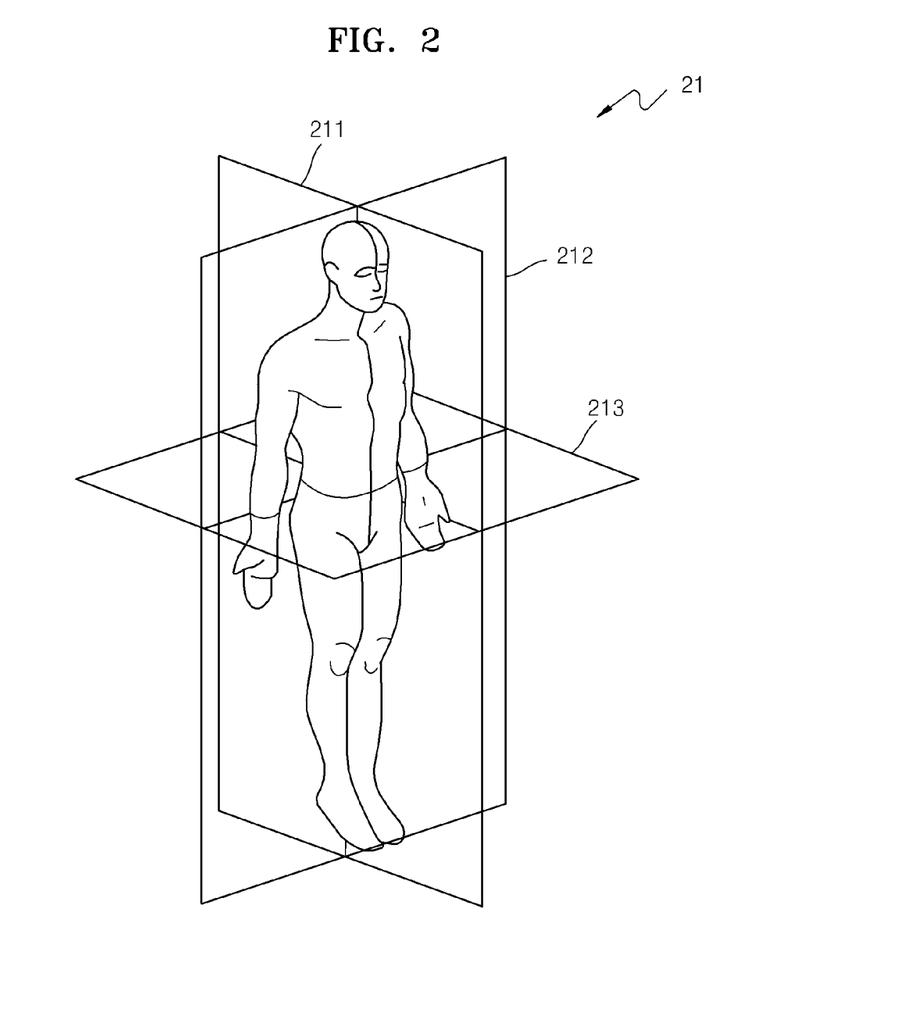
FIG. 2 shows an example of a standard plane, according to an embodiment of the present invention.

FIG. 2 shows an example of a standard plane, according to an embodiment of the present invention. In FIG. 2, a case where an object is a human body is shown, for convenience of description. FIG. 2 shows a drawing 21 indicating an object including a sagittal plane 211, a coronal plane 212, and an axial plane 213. In this case, the axial plane 213 may be a transverse plane.

For example, the sagittal plane 211 indicates a side of the object. The sagittal plane 211 may include a sagittal cross sectional plane. In more detail, the sagittal plane 211 indicates a plane that divides the object between left region and right region.

For example, the coronal plane 212 indicates the front of the object. In more detail, the coronal plane 212 indicates a plane that vertically divides the brain with reference to the front of the object. In this case, the front of the object may mean a face.

For example, the axial plane 213 indicates a cross section of the object. In more detail, the axial plane 213 is a plane that horizontally divides the object. In detail, the axial plane 213 indicates a plane that divides the object between upper region and lower region.

According to the present embodiment, the standard plane may further include other planes in addition to the sagittal plane 211, the coronal plane 212, and the axial plane 213.

In addition, FIG. 2 shows a single sagittal plane 211, a single coronal plane 212, and a single axial plane 213 only, but the present invention is not limited thereto.

Planes that are in parallel to the sagittal plane 211, the coronal plane 212, and the axial plane 213 may be included in the sagittal plane 211, the coronal plane 212, and the axial plane 213 respectively.

Figure 3:
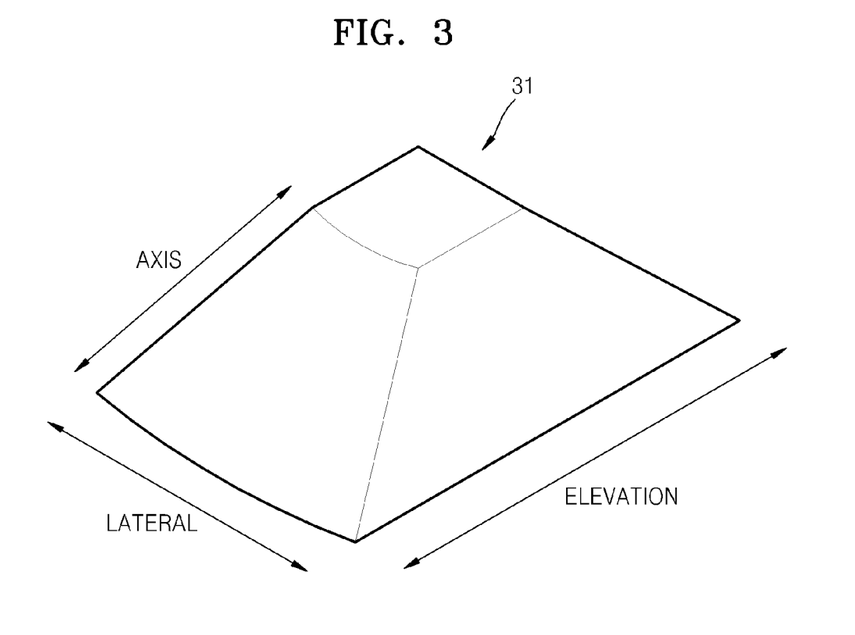
FIG. 3 is a diagram for describing a method of generating a standard image in the a standard image generating unit of FIG. 1, according to an embodiment of the present invention.

FIG. 3 is a diagram for describing a method of generating a standard image in the standard image generating unit 120 of FIG. 1, according to an embodiment of the present invention. Hereinafter, the method will be described with reference to FIGS. 1 and 3. For convenience of description, FIG. 3 shows a case where the image data acquiring unit 110 acquires three-dimensional (3D) image data by using a two-dimensional (2D) array probe, but the present invention is not limited thereto.

Ultrasound image data 31 may be acquired from an echo signal that is reflected from an object. In more detail, the ultrasound image data 31 may be formed by performing receive beamforming on the echo signal that is reflected from the object.

Thus, the ultrasound image data 31 is formed with respect to an axial direction indicating a propagation direction of an ultrasound signal, a lateral direction indicating a moving direction of a scan line, and an elevation direction indicating a depth direction of an ultrasound image.

Thus, the standard image generating unit 120 performs an image registration process on the ultrasound image data 31 based on a reference image to generate a standard image. That is, the standard image generating unit 120 generates the standard image from the ultrasound image data 31 based on the reference image by using an image registration algorithm.

For example, when an image registration algorithm for comparing the intensity of an image is used, the standard image generating unit 120 may compare the intensity of the reference image with the intensity of the ultrasound image data 31 and may generate the standard image having the most similar intensity to the reference image from the ultrasound image data 31.

For example, when an image registration algorithm for comparing the characteristics of an image is used, the standard image generating unit 120 may compare characteristics such as an edge or the like of the reference image with the characteristics of the ultrasound image data 31 and may generate the standard image having the most similar characteristics to the reference image from the ultrasound image data 31.

In this case, the standard image generating unit 120 may perform a modification process such as a synthesis process, an interpolation process, a translation process, a rotation process, a scaling process, or the like on the ultrasound image data 31 to generate the standard image.

Thus, the standard image generating unit 120 may generate the standard image of the object from the ultrasound image data 31 on which beamforming is performed. In this case, the standard image generating unit 120 may generate the standard image of the object without a loss in data.

The standard image generating unit 120 is not limited thereto and may generate the standard image of the object from a plurality of images that are scan-converted. That is, the standard image generating unit 120 may perform a modification process such as a synthesis process, an interpolation process, a translation process, a rotation process, a scaling process, or the like on the scan-converted plurality of images to generate a single standard image. In this case, the standard image generating unit 120 may generate the standard image at a higher speed than the case where the ultrasound image data 31 on which beamforming is performed is used.

Thus, the standard image generating unit 120 may generate the standard image by using the ultrasound image data 31 on which beamforming is performed or at least one of a plurality of images that are scan-converted. In this case, a user may select the ultrasound image data 31 on which beamforming is performed or at least one of a plurality of images that are scan-converted to generate the standard image.

Figure 4:
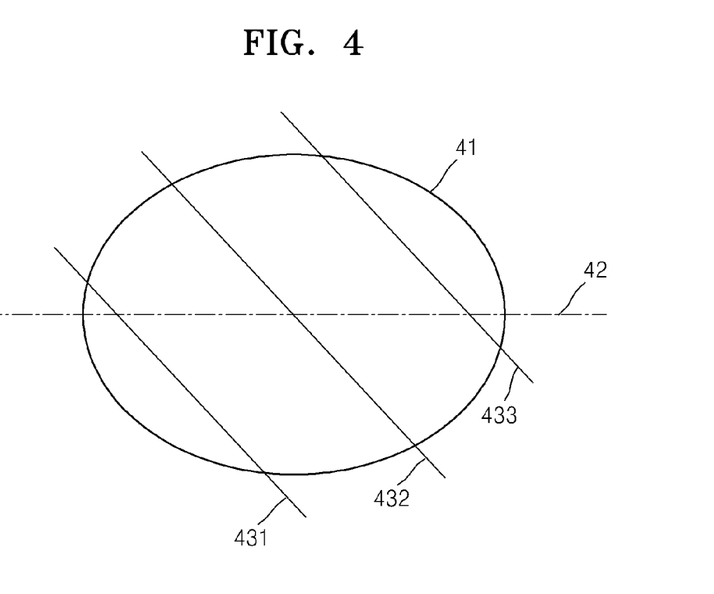
FIG. 4 is a diagram for describing a method of generating a standard image in the standard image generating unit of FIG. 1 according to another embodiment of the present invention.

FIG. 4 is a diagram for describing a method of generating a standard image in the standard image generating unit 120 of FIG. 1, according to another embodiment of the present invention. Hereinafter, the method will be described with reference to FIGS. 1 and 4.

FIG. 4 shows a standard plane 42 of an object 41. In this case, when the image data acquiring unit 110 acquires ultrasound image data with respect to a first plane 431, a second plane 432, and a third plane 433, the standard image generating unit 120 may generate an ultrasound standard image with respect to the standard plane 42 by using the ultrasound image data with respect to the first plane 431, the second plane 432, and the third plane 433.

FIG. 4 shows a case of a single standard plane 42, but the present invention is not limited thereto. The standard image generating unit 120 may generate standard images with respect to a plurality of standard planes, respectively.

Thus, when the image processing apparatus 100 is used, a standard image with respect to a standard plane may be acquired regardless of a user's manipulation of a probe, thereby improving the accuracy of reading an ultrasound image of the user.

Figure 5:
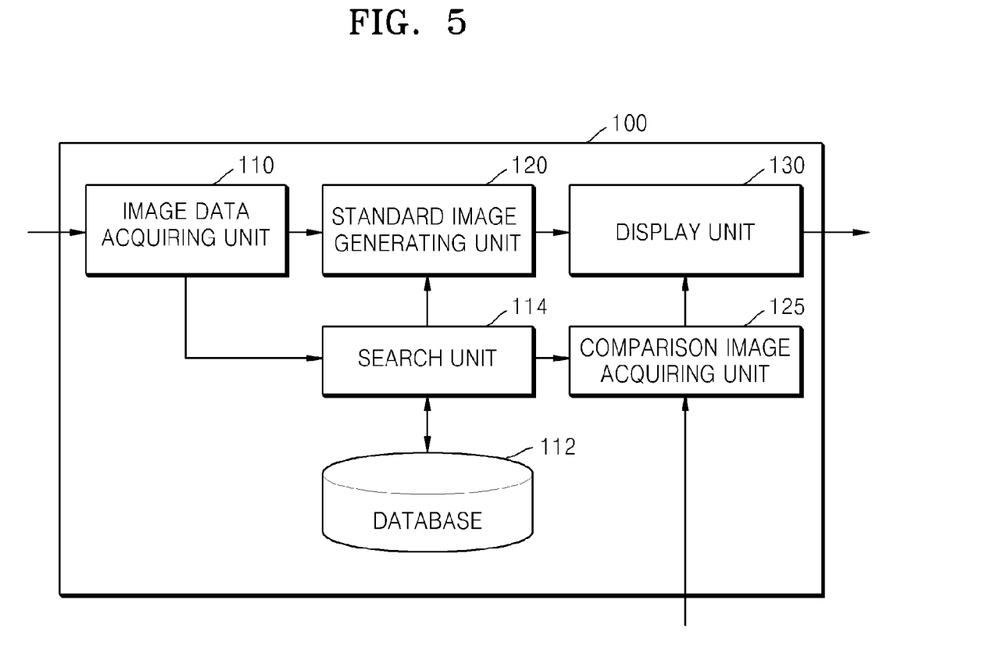
FIG. 5 is a block diagram of an image processing apparatus according to another embodiment of the present invention.

FIG. 5 is a block diagram of an image processing apparatus 100 according to another embodiment of the present invention. Referring to FIG. 5, the image processing apparatus 100 includes an image data acquiring unit 110, a database 112, a search unit 114, a standard image generating unit 120, a comparison image acquiring unit 125, and a display unit 130.

Elements related to the present embodiment are illustrated in FIG. 5. However, it will be understood by those of ordinary skill in the art that besides the elements illustrated in FIG. 5 other general elements may be further included.

The image processing apparatus 100 of FIG. 5 is an example of the image processing apparatus 100 of FIG. 1. Thus, the image processing apparatus 100 according to the present embodiment is not limited to including units of FIG. 5. Accordingly, although omitted, details described with reference to the image processing apparatus 100 of FIG. 1 are applied to the image processing apparatus 100 of FIG. 5.

According to the present embodiment, the image processing apparatus 100 processes an image of an object and provides the processed image to a user.

The image data acquiring unit 110 acquires ultrasound image data indicating information about the object.

The database 112 stores a reference image with respect to at least one standard plane, for each respective information about a human body and information about a region of the human body. In this case, the reference information stored in the database 112 may be a general image of an object without disease.

For example, the information about the human body may contain, but is not limited to, sex, height, age, or the like and the information about the human body region may contain, but is not limited to, a liver, breast, abdomen, brain, or the like. That is, the database 112 may store the reference image with respect to at least one standard plane for each of various information about the human bodies and various information about the human body regions.

The search unit 114 searches for a reference image corresponding to information about the human body and information about the human body region of the object.

For example, when the object is the heart of a thirty year-old woman, the search unit 114 searches for a reference image of the heart of the thirty year-old woman in the database 112. In addition, when information about height, weight, and the like of the object is recognized, the search unit 114 searches for the reference image in consideration of the information about the height, weight, and the like of the object.

In this case, information about the human body and information about the human body region of the object may be input by a user through a user interface unit (not shown), but the present invention is not limited thereto. That is, the information about the human body region may be recognized from image data acquired by the image data acquiring unit 110.

The standard image generating unit 120 generates an ultrasound standard image from the ultrasound image data, based on a reference image with respect to at least one standard image. For example, the standard image generating unit 120 generates the ultrasound standard image, based on the reference image that is found by the search unit 114.

Thus, the standard image generating unit 120 may generate a standard image in consideration of the human body information of the object, thereby further improving the accuracy of image registration.

The comparison image acquiring unit 125 acquires at least one comparison image indicating information about the object by using a diagnosis technique different from a diagnosis technique of acquiring the ultrasound image data.

Examples of the diagnosis technique different from a diagnosis technique of acquiring ultrasound image data may include a diagnosis technique using a magnetic resonance imaging (MRI) system, a diagnosis technique using a computed tomography (CT) system, and a diagnosis technique using a positron emission tomography (PET) system.

Thus, comparison image according to the present embodiment may include, but is not limited to, at least one of a MRI image, a CT image, and a PET image of the object.

The comparison image acquiring unit 125 may acquire the comparison image through a communication interface unit (not shown) from outside the image processing apparatus 100, but the present invention is not limited thereto. That is, the comparison image acquiring unit 125 may acquire the comparison image that is previously measured and is stored in the database 112.

The display unit 130 displays an ultrasound standard image. According to the present embodiment, the display unit 130 displays the ultrasound standard image together with at least one comparison image acquired by the compare image acquiring unit 125. In this case, each of the at least one comparison image and the ultrasound standard image, which are displayed by the display unit 130, may be images with respect to the same standard plane.

For example, when the display unit 130 displays a sagittal ultrasound standard image with respect to a sagittal plane of the object, at least one of a sagittal CT image, a sagittal MRI image, and a sagittal PET image with respect to the sagittal plane of the same object may be displayed together with a sagittal ultrasound standard image.

Thus, according to the present embodiment, the display unit 130 displays the ultrasound standard image together with at least one comparison image acquired by the comparison image acquiring unit 125. Alternatively, the display unit 130 may sequentially display the at least one comparison image and the ultrasound standard image on a single screen, or may display the at least one comparison image and the ultrasound standard image by converting one another in consideration of information input by a user.

In addition, the display unit 130 may sequentially display ultrasound standard images of the same object with a time interval. Thus, a change in the size of a tumor or the like may be easily traced.

Accordingly, the image processing apparatus 100 according to the present embodiment is used, thereby improving the accuracy of reading an ultrasound image by radiation oncologists, image medical scientists, or the like who are accustomed to a standard plane such as a sagittal plane, a coronal plane, an axial plane, or the like.

Figure 6:
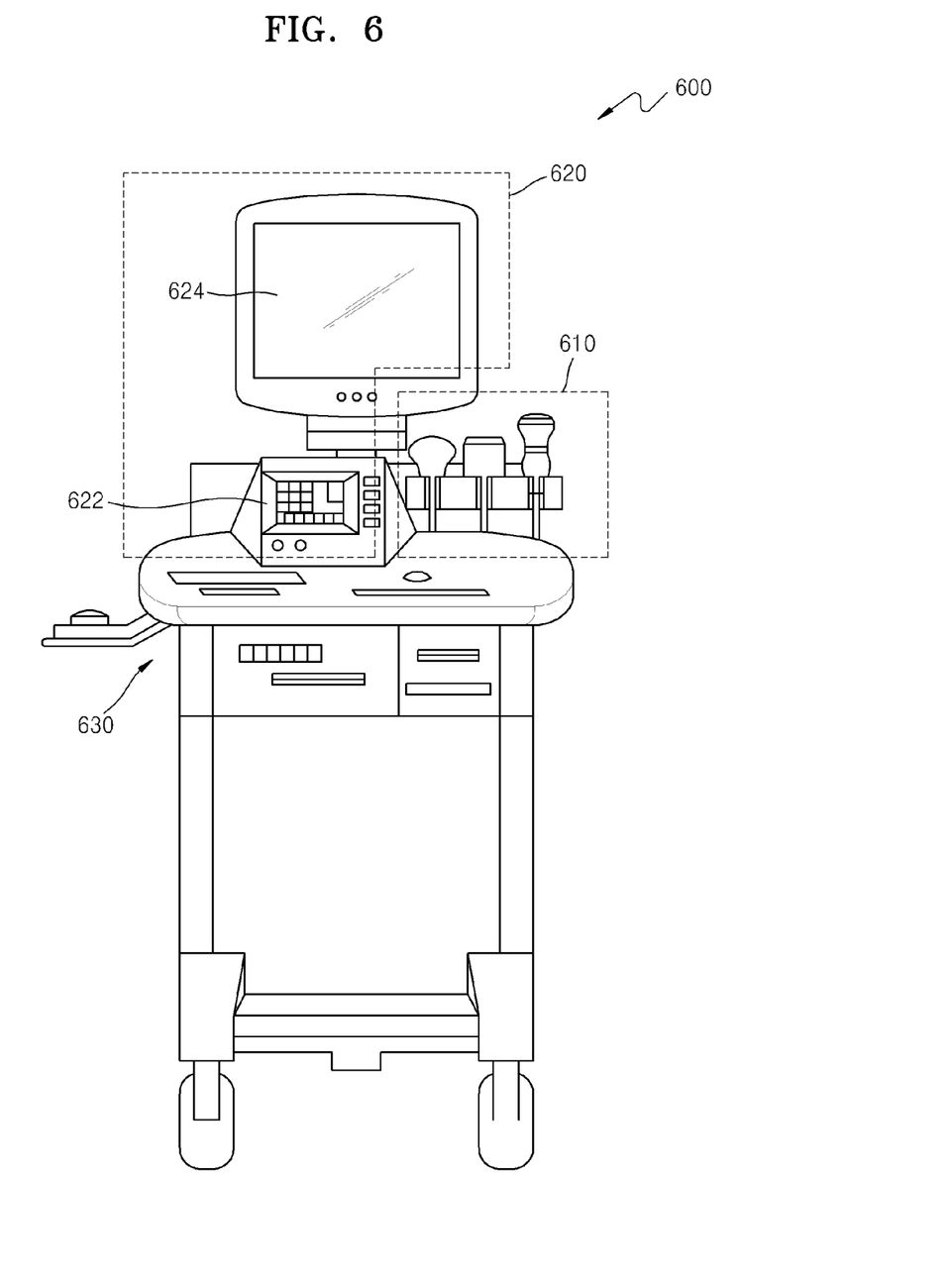
FIG. 6 is a diagram of an ultrasound diagnosis apparatus including an image processing apparatus, according to an embodiment of the present invention.

FIG. 6 is a diagram of an ultrasound diagnosis apparatus 600 including an image processing apparatus 100, according to an embodiment of the present invention. Referring to FIG. 6, the ultrasound diagnosis apparatus 600 includes a probe 610, a user interface unit 620, and a main system 630. The user interface unit 620 includes an input unit 622 and a display unit 624.

The ultrasound diagnosis apparatus 600 may be, but is not limited to, an apparatus that transmits an ultrasound signal to an object and generates an ultrasound image by using an echo signal that is reflected from the object. The ultrasound diagnosis apparatus 600 may include the image processing apparatus 100 shown in FIGS. 1 and 5. Accordingly, although omitted, details described with reference to the image processing apparatus 100 of FIGS. 1 and 5 are applied to the ultrasound diagnosis apparatus 600 of FIG. 6.

The probe 610 transmits the ultrasound signal to the object and receives the echo signal reflected from the object. The probe 610 shown in FIG. 6 may be, but is not limited to, an example of the image data acquiring unit 110 of the image processing apparatus 100 of FIGS. 1 and 5.

The user interface unit 620 acquires input information from a user and displays output information to the user. According to the present embodiment, the user interface unit 620 may include, but is not limited to, the input unit 622 and the display unit 624. That is, the user interface unit 620 may be embodied as a single unit having both input and output functions. The display unit 624 of FIG. 6 may be, but is not limited to, an example of the display unit 130 of the image processing apparatus 100 of FIGS. 1 and 5.

For example, the user interface unit 620 may include, but is not limited to, any input/output device included in the ultrasound diagnosis apparatus 600, such as a keyboard, a mouse, a touch panel, a speaker, or the like, and any software for driving the input/output device.

The main system 630 controls an overall function of the ultrasound diagnosis apparatus 600. That is, the main system 630 controls the probe 610 and the user interface unit 620. According to the present embodiment, the main system 630 may include the database 112, the search unit 114, the standard image generating unit 120, and the comparison image acquiring unit 125 of the image processing apparatus 100 of FIGS. 1 and 5.

Thus, the ultrasound diagnosis apparatus 600 may generate an ultrasound diagnosis image or an ultrasound standard image of the object. In addition, the ultrasound diagnosis apparatus 600 may display the ultrasound standard image together with at least one comparison image that is acquired by using a diagnosis technique different from a diagnosis technique of acquiring the ultrasound image data, thereby improving the accuracy of reading an image by the user.

Figure 7:
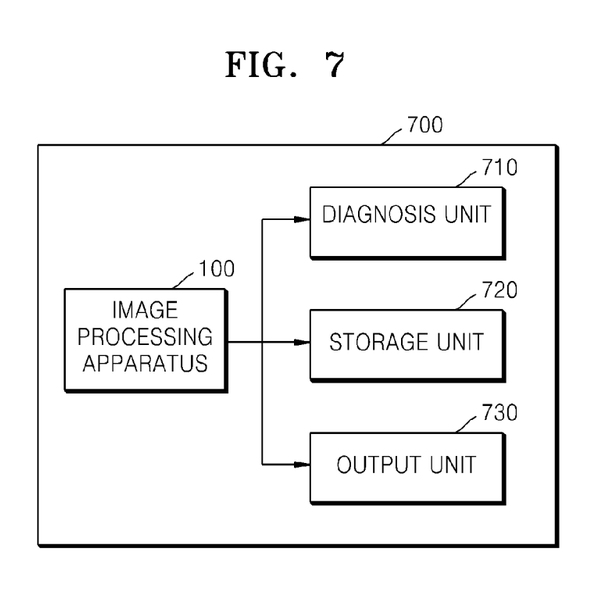
FIG. 7 is a block diagram of a medical image system including an image processing apparatus, according to an embodiment of the present invention.

FIG. 7 is a block diagram of a medical image system 700 including an image processing apparatus 100, according to an embodiment of the present invention. Referring to FIG. 7, the medical image system 700 includes the image processing apparatus 100, a diagnosis unit 710, a storage unit 720, and an output unit 730.

The image processing apparatus 100 of FIG. 7 corresponds to an example of the image processing apparatus 100 of FIGS. 1 and 5. Accordingly, although omitted here, details described with reference to the image processing apparatus 100 of FIGS. 1 and 5 are applied to the image processing apparatus 100 of FIG. 7.

The image processing apparatus 100 acquires ultrasound image data indicating information about an object and generates an ultrasound standard image of the ultrasound image data based on a reference image with respect to at least one standard plane. In addition, the image processing apparatus 100 acquires at least one comparison image indicating information about the object by using a diagnosis technique different from a diagnosis technique of acquiring the ultrasound image data. Thus, the image processing apparatus 100 may display the ultrasound standard image of the object together with the comparison image.

The diagnosis unit 710 performs a diagnosis technique different from a diagnosis technique of acquiring the ultrasound image data. According to the result of the diagnosis technique different from a diagnosis technique of acquiring ultrasound image data, the image processing apparatus 100 may acquire at least one comparison image indicating the information about the object.

For example, the diagnosis unit 710 may perform a diagnosis technique using a MRI system for acquiring a MRI image, a diagnosis technique using a CT system, a diagnosis technique using a PET system, and the like.

Thus, the image processing apparatus 100 may acquire at least one of a MRI image, a CT image, and a PET image of the object as the comparison image, through the diagnosis unit 710. In this case, the diagnosis unit 710 may perform diagnosis for acquiring the comparison image with respect to the same standard plane as that of the ultrasound standard image.

However, the present invention is not limited thereto. The medical image system 700 may acquire at least one of a MRI image, a CT image, and a PET image of the object, which are previously measured in an external device and stored. In this case, the external device may be a MRI system, a CT system, a PET system, or the like.

The storage unit 720 stores data that is generated during an operation of the medical image system 700. For example, the storage unit 720 may store data output from the image processing apparatus 100, a diagnosis image generated by the image processing apparatus 100, and the like.

According to the present embodiment, it will be understood by those of ordinary skill in the art that the storage unit 720 may be any storage device such as a hard disk drive (HDD), a read only memory (ROM), a random access memory (RAM), a flash memory, and a memory card.

The output unit 730 may transmit and receive data to and from an external device through a wired/wireless network or wired serial communication. In this case, examples of the network may include the Internet, a local area network (LAN), a wireless local area network (WLAN), a wide area network (WAN), a personal area network (PAN), or the like, but are not limited thereto. The network may be any type network that transmits and receives information.

Thus, the medical image system 700 may output the ultrasound standard image generated by the image processing apparatus 100 to an external device. Examples of the external device may include, but is not limited to, another medical image system which may be located at remote place, a fax machine, a general computer system, a PDA, or the like.

It will be understood by those of ordinary skill in the art that the storage unit 720 and the output unit 730 further include an image reading function and a searching function so as to be integrated in the form of a picture archiving communication system (PACS).

Figure 8:
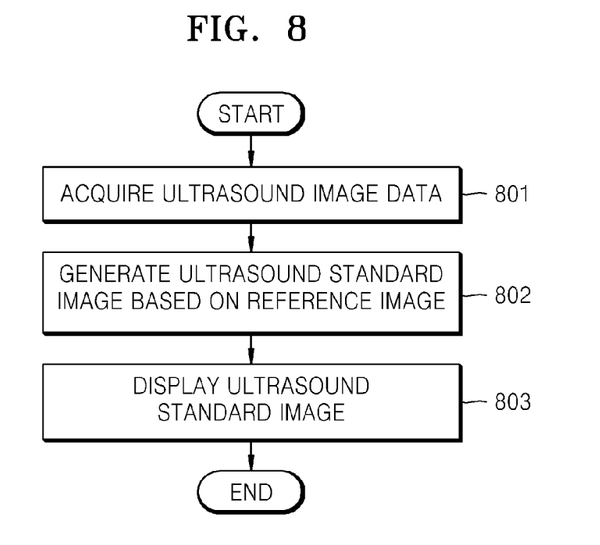
FIG. 8 is a flowchart of a method of processing an image, according to an embodiment of the present invention.

FIG. 8 is a flowchart of a method of processing an image, according to an embodiment of the present invention. Referring to FIG. 8, the method of processing the image includes time-series operations performed by the image processing apparatus 100, the ultrasound diagnosis apparatus 600, and the medical image system 700 shown in FIGS. 1, and 5 through 7. Accordingly, details described with reference to the image processing apparatus 100, the ultrasound diagnosis apparatus 600, and the medical image system 700 shown in FIGS. 1, and 5 through 7 are also applicable to the method of processing the image of FIG. 8.

In operation 801, the image data acquiring unit 110 acquires ultrasound image data indicating information about an object. For example, the image data acquiring unit 110 may acquire image data by using a probe.

In operation 802, the standard image generating unit 120 generates an ultrasound standard image from the ultrasound image data acquired in operation 801, based on a reference image with respect to at least one standard plane. In this case, the reference image may include at least one of a sagittal ultrasound image with respect to a sagittal plane, a coronal ultrasound image with respect to a coronal plane, and an axial ultrasound image with respect to an axial plane.

In operation 803, the display unit 130 displays the ultrasound standard image generated in operation 802. The display unit 130 may display the ultrasound standard image generated in operation 802 together with at least one comparison image acquired by using a diagnosis technique different from a diagnosis technique of acquiring the ultrasound image data.

When the method of processing the image according to the present embodiment is used, an ultrasound standard image with respect to a standard plane may be displayed, thereby improving the accuracy of reading an ultrasound image. In addition, an ultrasound diagnosis image and at least one comparison image that is acquired by using a diagnosis technique different from a diagnosis technique of acquiring the ultrasound image data may be viewed together, thereby improving the accuracy of diagnosis.

Figure 9:
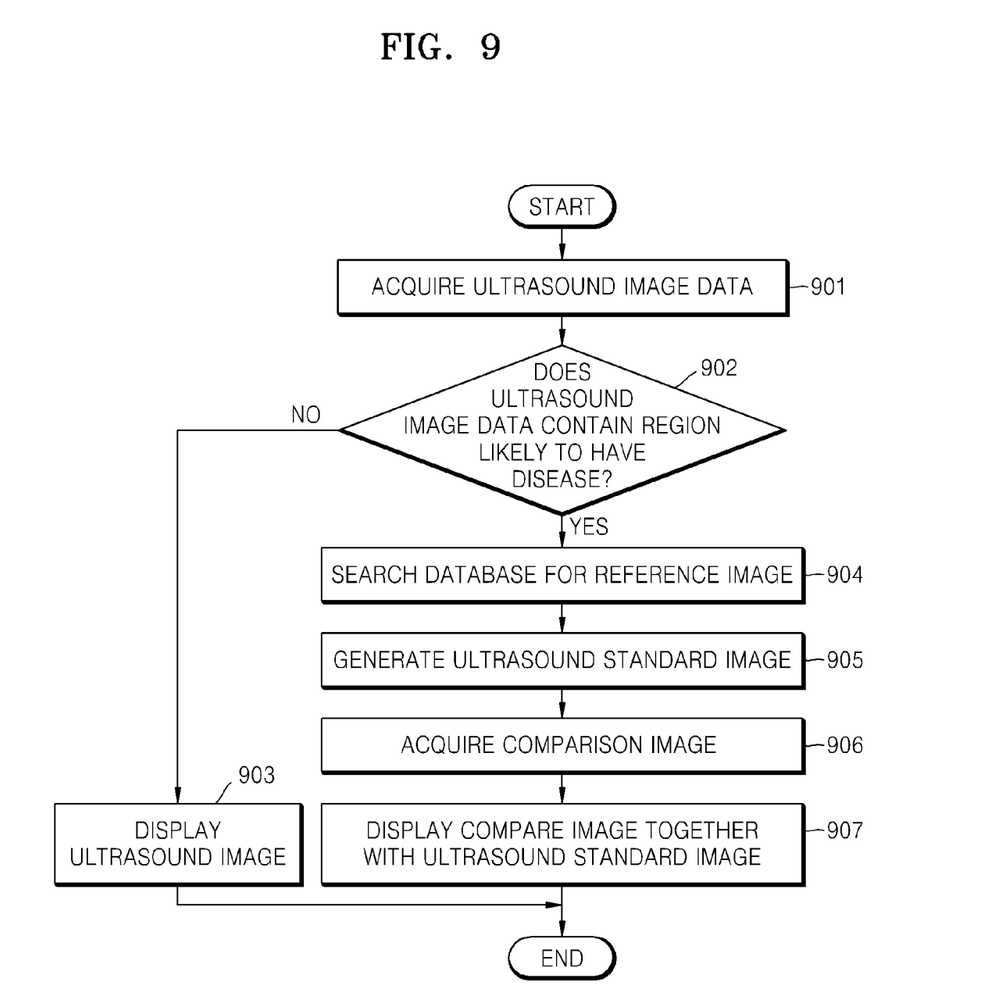
FIG. 9 is a flowchart of displaying an image, according to an embodiment of the present invention.

FIG. 9 is a flowchart of displaying an image, according to an embodiment of the present invention. Referring to FIG. 9, the method of displaying the image may include time-series operations performed by the image processing apparatus 100, the ultrasound diagnosis apparatus 600, and the medical image system 700 shown in FIGS. 1, and 5 through 7. Accordingly, although omitted, details described with reference to the image processing apparatus 100, the ultrasound diagnosis apparatus 600, and the medical image system 700 shown in FIGS. 1, and 5 through 7 are also applicable to the method of displaying the image of FIG. 9.

In operation 901, the image data acquiring unit 110 acquires ultrasound image data indicating information about an object.

In operation 902, the standard image generating unit 120 determines whether the ultrasound image data acquired in operation 901 contains a region that is likely to have a disease. According to the determination result, when the ultrasound image data does not contain the region that is likely to have a disease, the method proceeds to operation 903. When the ultrasound image data contains the region that is likely to have a disease, the method proceeds to operation 904.

In operation 903, the display unit 130 displays an ultrasound image. In this case, the ultrasound image may be generated from the ultrasound image data. However, according to a usage environment, when the ultrasound image data acquired in operation 901 does not contain the region that is likely to have a disease, the ultrasound image may not be displayed and the procedure may be finished. In this case, operation 903 may not be performed.

In operation 904, the search unit 114 searches the database 112 for a reference image corresponding to information about a human body and information about a region of the human body of the object. In this case, the database 112 stores a reference image with respect to at least one standard plane, for each respective information about the human body and information about the human body region.

In operation 905, the standard image generating unit 120 generates an ultrasound standard image from the ultrasound image data acquired in operation 901, based on the reference image that is searched for in operation 904.

In operation 906, the comparison image acquiring unit 125 acquires at least one comparison image indicating information about the object by using a diagnosis technique different from a diagnosis technique of acquiring the ultrasound image data in operation 901.

In operation 907, the display unit 130 displays the at least one comparison image acquired in operation 906 together with the ultrasound standard image generated in operation 905.

When the method of displaying the image according to the present embodiment is used, an ultrasound image of an object and at least one comparison image may be viewed simultaneously on a single screen, thereby improving the accuracy of reading an image and improving the correctness and accuracy of diagnosis.

The procedure shown in FIGS. 8 and 9 may be embodied in the forms of application program. Accordingly, the application may be executed in the form of a viewer in a general computer system, a PDA, a laptop computer, an ultrasound diagnosis apparatus, a medical image system, or the like. Thus, the user may conveniently use functions according to embodiments of the present invention.

In addition, the image processing apparatus 100, the ultrasound diagnosis apparatus 600, and the medical image system 700 display the ultrasound standard image and the comparison image, but the present invention is not limited thereto. That is, the ultrasound standard image may be uploaded to another diagnosis apparatus (e.g., a MRI system, a CT system, or a PET system).

For example, when a CT system obtains an ultrasound standard image, the accuracy of diagnosis of soft tissues that are barely viewable from a CT image may be improved. That is, the CT system displays the ultrasound standard image and a user reads the ultrasound standard image, thereby improving the accuracy of diagnosis.

Figure 10:
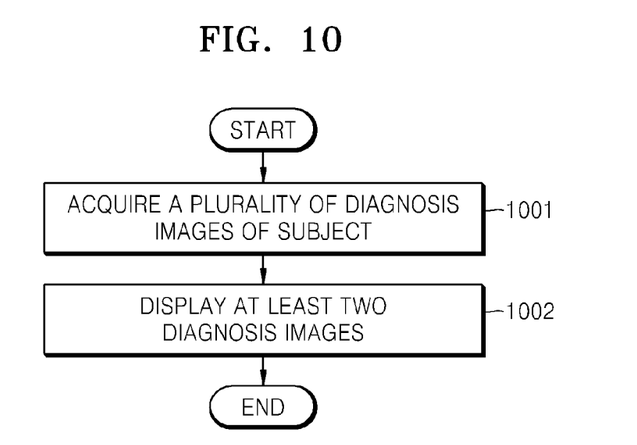
FIG. 10 is a flowchart of displaying a diagnosis image, according to an embodiment of the present invention.

FIG. 10 is a flowchart of displaying a diagnosis image, according to an embodiment of the present invention. Referring to FIG. 10, the method of displaying the diagnosis image includes time-series operations performed by the image processing apparatus 100, the ultrasound diagnosis apparatus 600, and the medical image system 700 shown in FIGS. 1, and 5 through 7. Accordingly, details described with reference to the image processing apparatus 100, the ultrasound diagnosis apparatus 600, and the medical image system 700 shown in FIGS. 1, and 5 through 7 are also applicable to the method of displaying the diagnosis image of FIG. 10.

In operation 1001, a diagnosis image viewer that is executed by a processor obtains a plurality of diagnosis images of an object, which are generated by at least two diagnosis apparatuses using different diagnosis techniques. For example, the diagnosis image viewer may receive a plurality of diagnosis images from at least two diagnosis apparatuses.

In this case, examples of the diagnosis apparatus may include an ultrasound system, a MRI system, a CT system, and a PET system. Examples of the diagnosis image may include an ultrasound image, an ultrasound standard image according to an embodiment of the present invention, a MRI image, a CT image, and a PET image.

In operation 1002, the diagnosis image viewer executed by the processor displays at least two diagnosis images together from among the plurality of diagnosis images obtained in operation 1001. In this case, the at least two diagnosis images may be selected by a user. In addition, the at least two diagnosis images may be obtained by using different diagnosis techniques, but are not limited thereto. That is, the at least two diagnosis images may be obtained by using the same diagnosis technique.

When diagnosis images obtained by using the same diagnosis technique are displayed together on a single screen, the diagnosis images obtained by using the same diagnosis technique may be obtained with respect to the same region of an object with a time interval, or may be obtained with respect to different regions of the object.

The diagnosis image viewer according to the present embodiment may be embodied in the form of application program by executing a processor included in a general computer system, a PDA, a laptop computer, a medical image system, or the like. Thus, a user may conveniently diagnose the object by using the diagnosis image viewer.

As described above, an ultrasound standard image may be generated and displayed, different ultrasound images may not be obtained with respect to the same region of interest according to the user's manipulation of a probe, thereby improving the accuracy of diagnosis and the accuracy of reading an image of a user who views the ultrasound image.

In addition, since the user views both the ultrasound standard image and the comparison image with respect to the same plane together, whether a disease exists may be easily determined by comparing a plurality of images of a region that is anatomically located at the same place.

The embodiments of the present invention may be written as computer programs and can be implemented in general-use digital computers that execute the programs using a computer readable recording medium. In addition, a structure of data used in the above-described method may be recorded in a computer readable recording medium through various methods. Examples of the computer readable recording medium include magnetic storage media (e.g., ROMs, RAMs, universal serial buses (USBs), floppy disks, hard disks, etc.), optical recording media (e.g., CD-ROMs, or DVDs), and storage media such as PC interfaces (e.g., PCI, PCI-express, Wifi, etc.).

As described above, an ultrasound standard image may be generated and displayed, different ultrasound images may not be obtained with respect to the same region of interest according to the user's manipulation of a probe, thereby improving the accuracy of diagnosis and the accuracy of reading an image of a user who searches for the ultrasound image.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An image processing apparatus, comprising:
   an image data acquiring unit for acquiring ultrasound image data indicating information about an object;
   a database for storing a plurality of ultrasound reference images with respect to at least one standard plane, for information about human body regions;
   a search unit for recognizing information about a human body region of the object from the ultrasound image data, and searching for an ultrasound reference image, among the plurality of ultrasound reference images, corresponding to the recognized information about the human body region of the object;
   a standard image generating unit for generating an ultrasound standard image based on the recognized information about a human body region of the object from the ultrasound image data, regardless of a user's manipulation of probe orientation, by performing an image registration process on the ultrasound image data with the searched ultrasound reference image; and
   a display unit for displaying the generated ultrasound standard image.

2. The image processing apparatus of claim 1, wherein the plurality of ultrasound reference images comprise at least one of a sagittal ultrasound image with
   respect to a sagittal plane, a coronal ultrasound image with respect to a coronal plane, and an axial ultrasound image with respect to an axial plane.

3. The image processing apparatus of claim 1, further comprising a comparison image acquiring unit for acquiring at least one comparison image indicating the information about the object by using a diagnosis technique different from a diagnosis technique of acquiring the ultrasound image data, wherein the display unit displays the acquired at least one comparison image together with the ultrasound standard image.

4. The image processing apparatus of claim 3, wherein the at least one comparison image comprises at least one of a magnetic resonance imaging (MRI) image, a computed tomography (CT) image, and a positron emission tomography (PET) image of the object.

5. The image processing apparatus of claim 3, wherein each of the acquired at least one comparison image and the ultrasound standard image, which are displayed together by the display unit, is an image with respect to the same standard plane.

6. The image processing apparatus of claim 1, wherein the standard image generating unit generates the ultrasound standard image according to whether the acquired ultrasound image data contains a region that is likely to have a disease.

7. An ultrasound diagnosis apparatus, comprising:
   a probe for acquiring ultrasound image data indicating information about an object;
   a database for storing a plurality of ultrasound reference images with respect to at least one standard plane, for information about human body regions;
   a search unit for recognizing information about a human body region of the object from the ultrasound image data, and searching for an ultrasound reference image, among the plurality of ultrasound reference images, corresponding to the recognized information about the human body region of the object;
   a main system for generating an ultrasound standard image based on the recognized information about a human body region of the object from the ultrasound image data, regardless of a user's manipulation of probe orientation, by performing an image registration process on the ultrasound image data with the searched ultrasound reference image; and a display unit for displaying the generated ultrasound standard image.

8. The ultrasound diagnosis apparatus of claim 7, wherein the main system acquires at least one comparison image indicating the information about the object by using a different diagnosis technique from a diagnosis technique of acquiring the ultrasound image data, wherein the display unit displays the at least one comparison image together with the ultrasound standard image.

9. A medical image system, comprising:

an image processing apparatus for acquiring ultrasound image data indicating information about an object, for recognizing information about a human body region of the object from the ultrasound image data, for searching for an ultrasound reference image corresponding to the recognized information about the human body region of the object among a plurality of ultrasound reference images stored in a database, and for generating an ultrasound standard image based on the recognized information about a human body region of the object from the ultrasound image data, regardless of a user's manipulation of probe orientation, by performing an image registration process on the ultrasound image data with the searched ultrasound reference image; and a diagnosis unit for performing a diagnosis technique different from a diagnosis technique of acquiring the ultrasound image data, wherein the image processing apparatus displays the generated ultrasound standard image together with at least one comparison image that is generated by using the diagnosis technique different from the diagnosis technique of acquiring the ultrasound image data.

10. A method of processing an image, comprising:

storing a plurality of ultrasound reference images with respect to at least one standard plane, for information about human body regions, in data;

acquiring ultrasound image data indicating information about an object;

recognizing information about a human body region of the object from the ultrasound image data;

searching the database for an ultrasound reference image, among the plurality of ultrasound reference images, corresponding to the recognized information about the human body region of the object;

generating an ultrasound standard image based on the recognized information about a human body region of the object from the ultrasound image data, regardless of a user's manipulation of probe orientation, by performing an image registration process on the acquired ultrasound image data with the searched ultrasound reference image; and displaying the generated ultrasound standard image.

11. The method of claim 10, wherein the plurality of ultrasound reference images comprise at least one of a sagittal ultrasound image with respect to a sagittal plane, a coronal ultrasound image with respect to a coronal plane, and an axial ultrasound image with respect to an axial plane.

12. The method of claim 10, further comprising:

acquiring at least one comparison image indicating the information about the object by using a diagnosis technique different from a diagnosis technique of acquiring the ultrasound image data; and displaying the acquired at least one comparison image together with the ultrasound standard image.

13. The method of claim 12, wherein the at least one comparison image comprises at least one of a magnetic resonance imaging (MRI), a computed tomography (CT) image, and a positron emission tomography (PET) image of the object.

14. The method of claim 12, wherein each of the at least one comparison image and the ultrasound standard image, which are displayed together, is an image with respect to the same standard plane.

15. A non-transitory computer readable recording medium having recorded thereon a program for executing the method of claim 10.

* * * * *